US011123533B2

(12) United States Patent
Zindel et al.

(10) Patent No.: US 11,123,533 B2
(45) Date of Patent: Sep. 21, 2021

(54) MEDICAL FLUID CONNECTION DEVICE

(71) Applicant: B. BRAUN MELSUNGEN AG, Melsungen (DE)

(72) Inventors: Steffen Zindel, Wehretal (DE); Viet Minh Duc Le, Melsungen (DE)

(73) Assignee: B. BRAUN MELSUNGEN AG, Melsungen (DE)

( * ) Notice: Subject to any disclaimer, the term of this patent is extended or adjusted under 35 U.S.C. 154(b) by 515 days.

(21) Appl. No.: 16/018,779

(22) Filed: Jun. 26, 2018

(65) Prior Publication Data

US 2018/0369557 A1   Dec. 27, 2018

(30) Foreign Application Priority Data

Jun. 27, 2017   (DE) .......................... 102017210795.2

(51) Int. Cl.
*A61M 39/26* (2006.01)
*A61M 39/10* (2006.01)
*A61M 39/24* (2006.01)

(52) U.S. Cl.
CPC ............ *A61M 39/10* (2013.01); *A61M 39/24* (2013.01); *A61M 39/26* (2013.01); *A61M 2039/2433* (2013.01); *A61M 2039/2473* (2013.01); *A61M 2205/0216* (2013.01)

(58) Field of Classification Search
CPC ............ A61M 39/26; A61M 2039/266; A61M 2039/267; A61M 2039/2433; A61M 2039/1066; A61M 2039/1033
See application file for complete search history.

(56) References Cited

U.S. PATENT DOCUMENTS

| 5,492,147 A * | 2/1996 | Challender | ........... A61M 39/26 137/614.05 |
| 7,350,764 B2 * | 4/2008 | Raybuck | ............... A61M 39/26 251/149.1 |
| 7,470,262 B2 | 12/2008 | Hiejima et al. | |

(Continued)

FOREIGN PATENT DOCUMENTS

WO   2010028040 A1   3/2010

OTHER PUBLICATIONS

German Search Report for German Application No. 10 2017 210 795.2, dated Feb. 28, 2018, with partial translation, 9 pages.

(Continued)

*Primary Examiner* — David Bochna

(57) ABSTRACT

A medical fluid connection device connects to a complementary connector unit in a fluid-conducting manner. The medical fluid connection device has a housing member having an inlet opening and at least one outlet opening. The inlet opening and at least one outlet opening are interconnected in a fluid-conducting manner by a fluid duct that extends substantially along an axial direction, and a soft elastic sealing member which in a circumferential direction at least in portions encompasses a wall of the fluid duct and along the axial direction is guided so as to be movable in relation to the wall of the fluid duct. A Luer external taper connects to a Luer internal taper of the complementary connector unit in a fluid-tight manner. The Luer external taper is configured by a wall portion of the soft elastic sealing member. The medical fluid connection device can be used in infusion therapy.

11 Claims, 7 Drawing Sheets

(56) References Cited

U.S. PATENT DOCUMENTS

Figure 1:
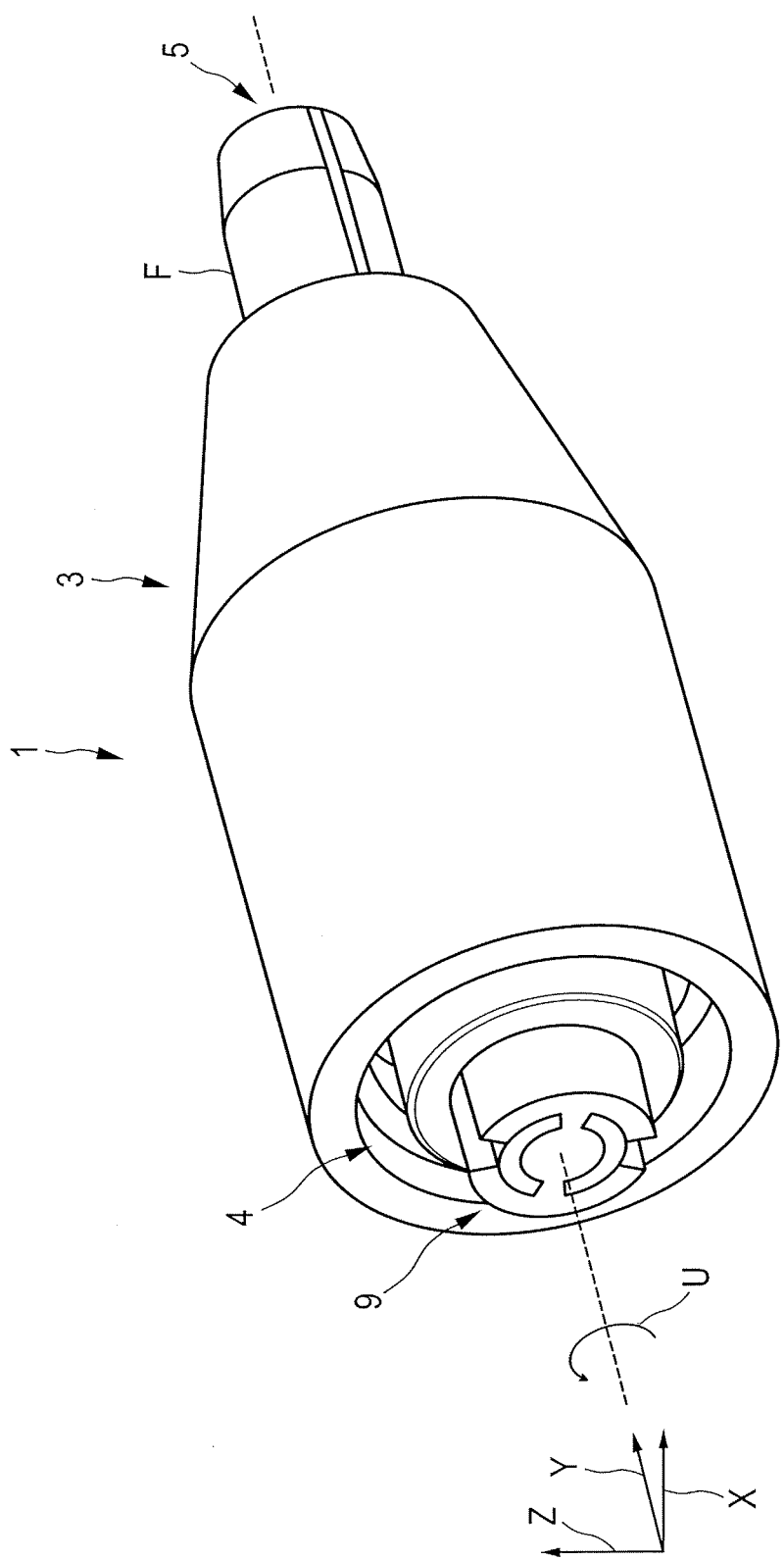

| | | | |
|---|---|---|---|
| 2003/0060804 A1* | 3/2003 | Vaillancourt | A61M 39/26 604/533 |
| 2003/0136932 A1* | 7/2003 | Doyle | A61M 39/26 251/149.1 |
| 2005/0087715 A1* | 4/2005 | Doyle | A61M 39/26 251/149.1 |
| 2006/0157971 A1* | 7/2006 | Baldwin | A61M 39/26 285/3 |
| 2007/0066965 A1* | 3/2007 | Coambs | A61M 39/26 604/533 |
| 2008/0287920 A1* | 11/2008 | Fangrow | A61M 39/26 604/535 |
| 2010/0063482 A1* | 3/2010 | Mansour | A61M 39/26 604/539 |
| 2014/0371724 A1 | 12/2014 | Tsai | |
| 2015/0073380 A1 | 3/2015 | Mansour et al. | |
| 2015/0102245 A1* | 4/2015 | Chen | A61M 39/10 251/149 |
| 2016/0228687 A1* | 8/2016 | Chih | A61M 39/26 |
| 2017/0028187 A1 | 2/2017 | Mansour et al. | |

OTHER PUBLICATIONS

European Search Report for European Application No. 18176594.2, dated Aug. 12, 2018, 8 pages.

\* cited by examiner

MEDICAL FLUID CONNECTION DEVICE

CROSS REFERENCE TO RELATED APPLICATION(S)

This application claims the benefit of priority of German patent application no. DE 10 2017 210 795.2, filed Jun. 27, 2017, the content of which is hereby incorporated by reference into this application in its entirety.

FIELD

The present disclosure relates generally to medical fluid connection devices, and in particular to a medical fluid connection device for connecting in a fluid-conducting manner to a complementary connector unit, which may have a housing member having an inlet opening and at least one outlet opening, said inlet opening and said at least one outlet opening being interconnected in a fluid-conducting manner by way of a fluid duct that extends substantially along an axial direction, and a soft elastic sealing member which in a circumferential direction at least in portions encompasses a wall of the fluid duct and along the axial direction is guided so as to be movable in relation to the wall of the fluid duct, wherein the sealing member in a non-connected state of the fluid connection device may assume a sealing position and seals in a fluid-tight manner the at least one outlet opening and, in a state of the fluid connection device connected to the complementary connector unit, along the axial direction is elastically compressed to a compression position in such a manner that the at least one outlet opening is released, wherein a Luer external taper may be provided for connecting in a fluid-tight manner to a Luer internal taper of the complementary connector unit.

BACKGROUND

A medical fluid connection device is known from WO 2010/028040 A1. The known medical fluid connection device is provided for connecting in a fluid-conducting manner medical hose portions, for example in an infusion therapy, and has a housing member having a main member and a thread-supporting closure part. The housing member has an inlet opening which by way of a fluid duct that extends along an axial direction is connected in a fluid-conducting manner to two outlet openings disposed at the end side. The fluid duct is configured so as to be tubular, wherein the outlet openings, in each case in the form of a radial bore, extend through a wall of the fluid duct. A soft elastic, elongate sealing member is provided so as to encompass the wall of the fluid duct in a circumferential direction. The sealing member in a sealing position seals the outlet openings in a fluid-tight manner. In a state of the fluid connection device connected to a complementary connector unit, the sealing member on the wall of the fluid duct is compressed along the axial direction to a compression position and in this manner releases the outlet openings. The housing member has a Luer external taper which is provided for receiving in a fluid-tight manner a Luer internal taper of the complementary connector unit. The Luer external taper is configured by a corresponding conical design embodiment of an end-side region of the wall of the fluid duct.

SUMMARY

It is an object of the present disclosure to achieve a medical fluid connection device of the type which in comparison to the prior art has improved properties.

This object is achieved in that the Luer external taper is configured by a wall portion of the soft elastic sealing member. A design embodiment of the fluid connection device that is adapted to the functionality and the production is achieved by the solution according to the present disclosure, on the one hand. This is because a conical design embodiment of the wall of the fluid duct in order for the Luer external taper to be configured can be dispensed with. In this manner, a particularly free-moving mobility of the sealing member between the sealing position and the compression position can be achieved, since an effect of an axial force and/or a circumferential force on the sealing member that would otherwise usually arise herein—effected by a conical design embodiment of the wall of the fluid duct—is avoided. On the other hand, the solution according to the present disclosure permits an improved tightness of the Luer connection between the fluid connection device and the complementary connector unit. This is because the Luer external taper is configured on the soft elastic sealing member. In this manner, any potential tolerances of the Luer connection in terms of shape and/or position between the fluid connection device and the connector unit can be compensated for by means of an elastic deformation of the sealing member. Any leakage can be avoided in this manner. The wall of the fluid duct can be configured in the form of an elongate hollow cylinder, a tube, a sleeve, or the like. An external wall face of the wall of the fluid duct can advantageously be configured in the form of a substantially straight circular-cylindrical area. The soft elastic sealing member can have a sleeve-type or tubular basic shape. An internal wall face of the sealing member can at least in portions be advantageously fixed to the external wall face of the fluid duct in the radial direction. To this extent, the sealing member in a repositioning between the sealing position and the compression position can be supported in the radial direction on the wall of the fluid duct and be guided so as to slide in the axial direction. The sealing member can have a material composition which includes an elastomer, in particular a silicone rubber. The sealing member is advantageously designed in such a manner that said sealing member, after having been deformed from the sealing position to the compression position, and after the removal of the complementary connector unit, elastically springs back to the sealing position, wherein the outlet opening is sealed in a self-acting manner and a fluid path through the fluid connection device is thus closed in a self-acting manner. The directional indications of the axial direction, the radial direction, and the circumferential direction used in this description relate to a coordinate system, the axial component of the latter being oriented so as to be coaxial or parallel with a longitudinal axis of the fluid connection device.

In one embodiment, the sealing member has at least one passage opening which in the compression position in relation to the at least one outlet opening is disposed so as to at least in portions overlap in such a manner that said at least one outlet opening is released at least in portions, causing a fluid-conducting connection between the inlet opening and the passage opening. Accordingly, in the compression position of the sealing member a fluid path that extends through the fluid connection device is released such that a respective fluid, for instance an infusion solution, can flow between the inlet opening, the outlet opening, and the passage opening. The at least one passage opening can advantageously be disposed so as to be contiguous to the Luer external taper. This design embodiment of the present disclosure permits sealing of the fluid path through the fluid connection device in a particularly functionally reliable manner.

In a further embodiment, the at least one passage opening is configured in the design of a passage slot, and/or the at least one outlet opening is configured in the design of an outlet slot. The passage slot and/or the outlet slot can advantageously extend substantially along the axial direction. The passage slot along the circumferential direction thereof can be bordered in a completely encircling manner by respective wall portions of the sealing member, or be open at least at one end side of said sealing member. At least two passage slots can advantageously be disposed so as to be mutually offset along the circumferential direction of the sealing member. Accordingly, at least two outlet slots can be advantageously provided.

In a further embodiment, the at least one outlet opening extends in a substantially radial manner through the wall of the fluid duct. Accordingly, the outlet opening is configured in the form of a radial opening. In as far as the outlet opening is configured in the design of an outlet slot, it is advantageous for the outlet slot to extend across at least 25% of the axial length of the wall of the fluid duct.

In a further embodiment, the sealing member has a closure portion which in a fluid-tight manner seals an end-side axial opening of the fluid duct. The fluid-tight sealing of the axial opening of the fluid duct in this manner is caused at least in the sealing position of the sealing member. The closure portion can advantageously be designed in such a manner that the axial opening moreover is sealed in a fluid-tight manner in the compression position and to this extent in a state connected to the complementary connector unit. The closure portion can be disposed so as to cover the axial opening at the end side and to this extent have an effective cross section which is larger than the cross section of the axial opening of the fluid duct. Alternatively, the closure portion can have an external diameter which corresponds substantially to an internal diameter of the axial opening of the fluid duct, wherein the fluid-tight sealing is caused by the closure portion in the radial direction bearing on an internal wall of the fluid duct.

In a further embodiment, the closure portion is configured in such a manner that said closure portion in a repositioning of the sealing member is movable in the fluid duct along the fluid duct between the sealing position and the compression position. The closure portion can be configured in the design of a stopple, a plug, a stopper, or the like. In a repositioning of the sealing member between the sealing position and the compression position, the closure portion can be movable in a sliding manner in the axial direction, and in the radial direction be supported in a fluid-tight manner on an internal wall of the fluid duct. This design embodiment of the present disclosure guarantees sealing of the axial opening of the fluid duct that is particularly functionally reliable.

In a further embodiment, the sealing member has a profiled portion which is connected in a form-fitting manner to a complementary profiled counter portion of the housing member in such a manner that the sealing member in the circumferential direction is fixed to the housing member, in particular to the wall of the fluid duct. It is advantageous for the profiled counter portion to be configured by a corresponding profiled feature of the wall of the fluid duct. The profiled counter portion can be configured in the design of a guide groove, the profiled portion accordingly being configured in the design of a complementary guide element, or vice versa. Any unintentional rotating of the sealing member in a repositioning between the sealing position and the compression position is counteracted as a result of the form-fitting connection in the circumferential direction between the profiled portion and the profiled counter portion. Consequently, this design embodiment of the present disclosure permits guiding of the sealing member in relation to the wall of the fluid duct in a manner that is particularly adapted to tolerances. A particularly reliable closing and opening of the fluid path that extends through the fluid connection device can be achieved in this manner.

In a further embodiment, the profiled portion has at least one sliding element which engages in a guide slot of the profiled counter portion. The sliding element can be configured in the form of a sliding strip, a sliding shoe, a sliding block, or the like. The guide slot can advantageously extend substantially along the axial direction. It is moreover advantageous for the guide slot to be incorporated in the wall of the fluid duct. Guiding of the sealing member in relation to the wall of the fluid duct in a manner that is particularly adapted to tolerances can be achieved when at least two sliding elements that are disposed so as to be mutually offset in the circumferential direction, and accordingly at least two guide slots that are disposed so as to be mutually offset in the circumferential direction, are provided.

The fluid duct has a receptacle portion which is provided for receiving an elongate receptacle appendage of the complementary connector unit. The receptacle portion can comprise a wall portion of the internal wall of the fluid duct. The receptacle appendage can be configured in the form of a spike, a pin, a tube, or the like. The receptacle portion can advantageously comprise an end-side portion of the fluid duct. This design embodiment of the present disclosure permits a mutual alignment of the fluid connection device and of the complementary connector unit that is particularly adapted to tolerances, such that an alignment of the Luer external taper in relation to the Luer internal taper that is particularly adapted to tolerances is accordingly achieved. Unintentional leakages can be avoided in this manner.

In a further embodiment, the housing member has a threaded portion, in particular in the design of an internal thread, which is provided for connecting to a threaded counter portion, in particular in the form of an external thread, of the complementary connector unit. The threaded portion can be configured in the design of a threaded bore which is immovable in relation to the housing member, or in the design of a union nut, a threaded sleeve, or the like, that is movable in relation to the housing member. Any unintentional releasing of the connection between the Luer external taper and the Luer internal taper is counteracted on account of this design embodiment of the present disclosure.

The object on which this disclosure is based is also achieved in that the fluid connection device is composed of the sealing member and the housing member. To this extent, the fluid connection device can be composed of only two components, specifically the sealing member and the housing member. A particularly simple and cost-effective production can be achieved on account of the reduction of the number of components in this manner.

BRIEF DESCRIPTION OF THE DRAWING FIGURES

Figure 2A:
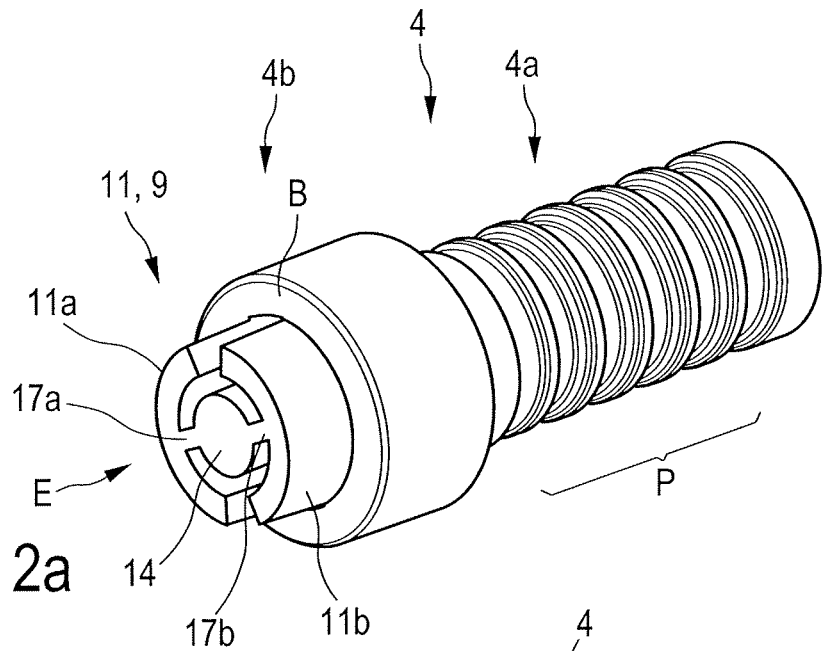
Figure 2B:
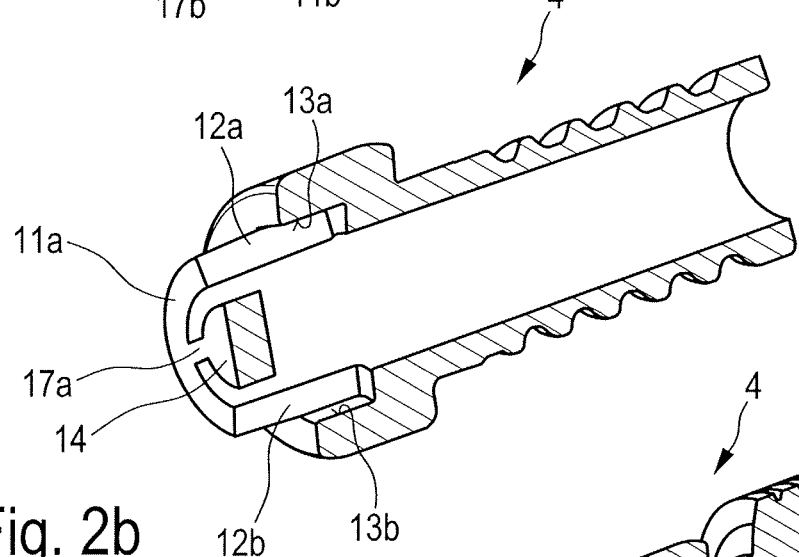
Figure 2C:
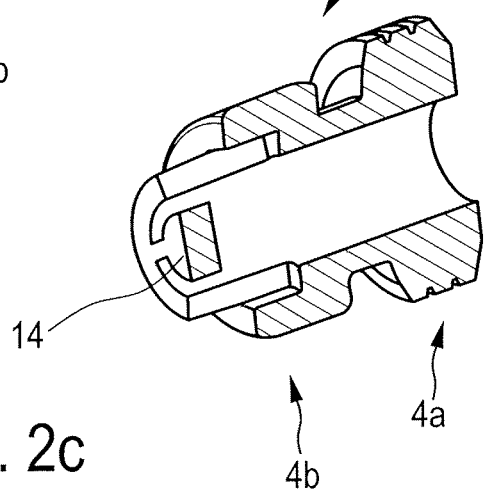
Figure 3A:
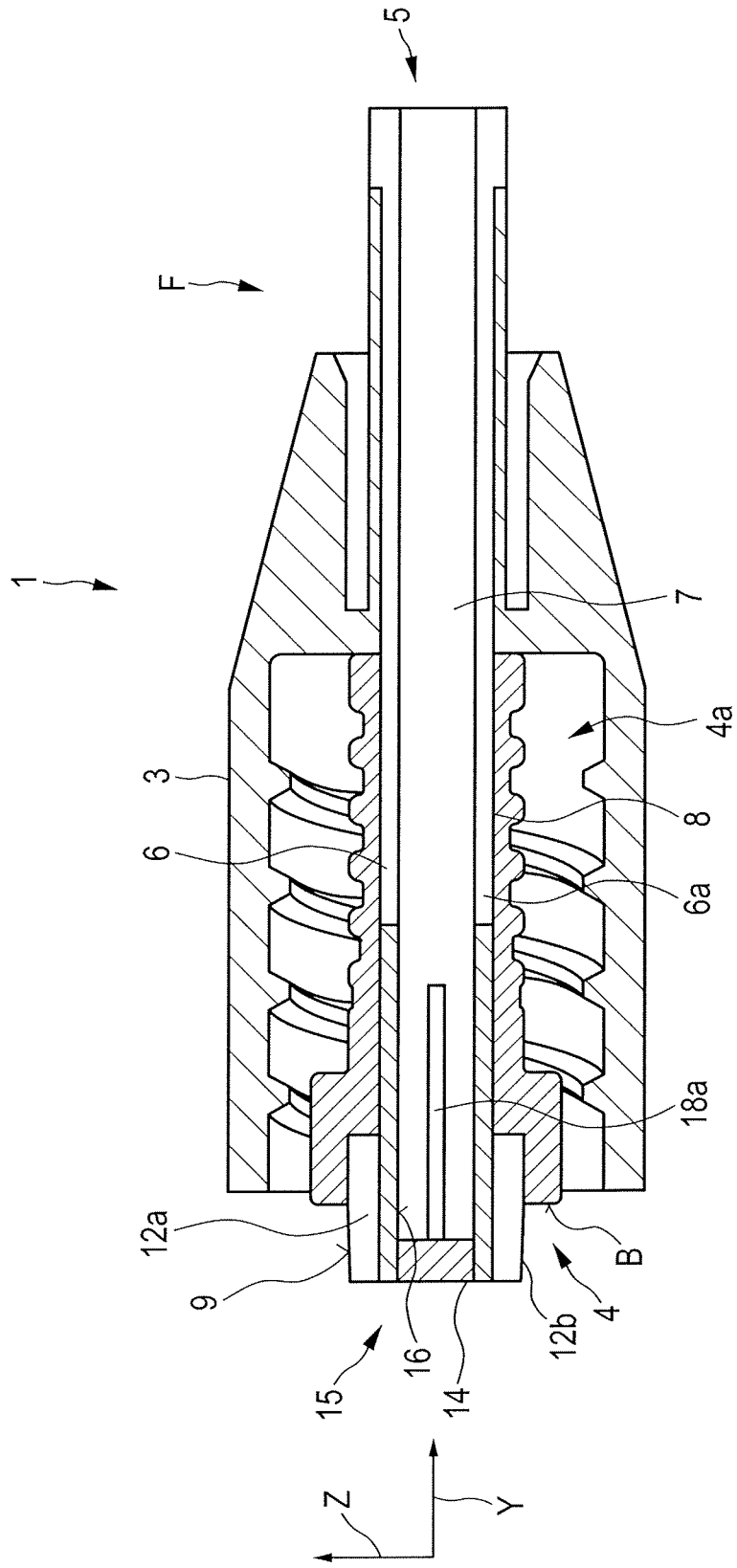
Figure 3B:
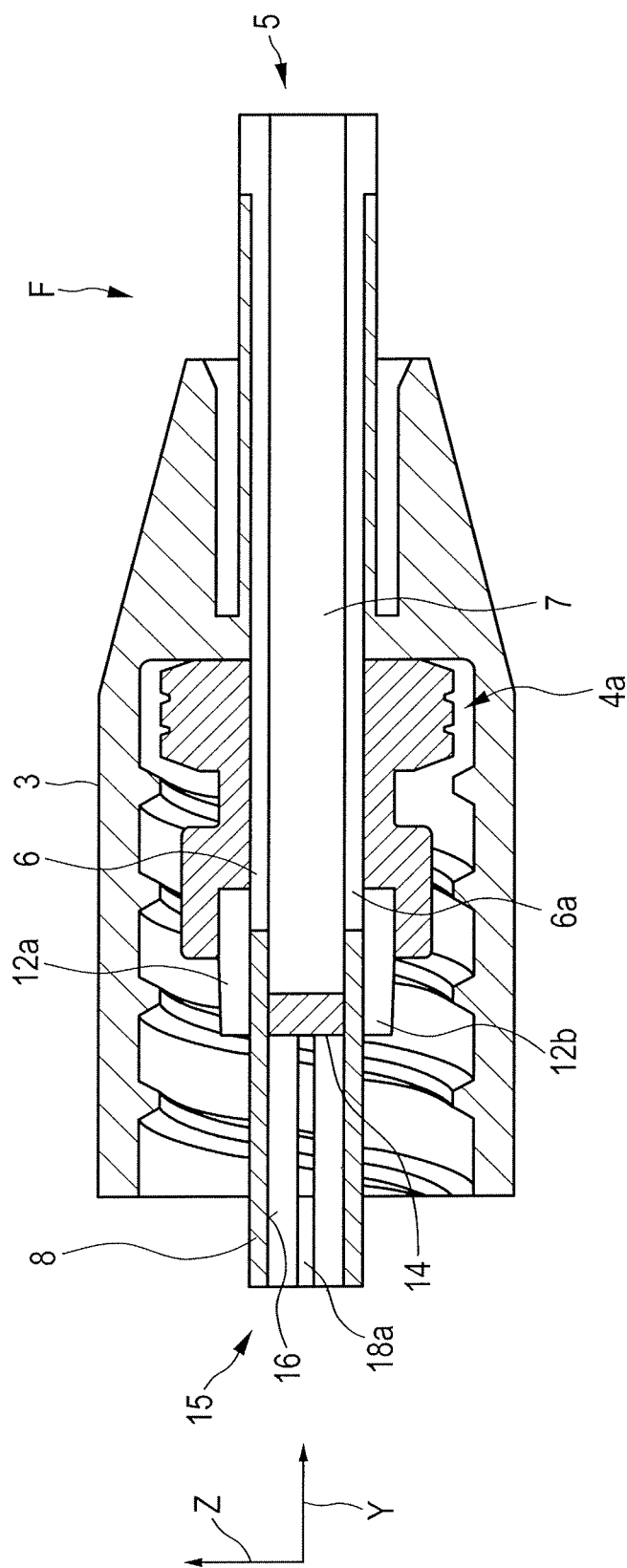
Figure 4A:
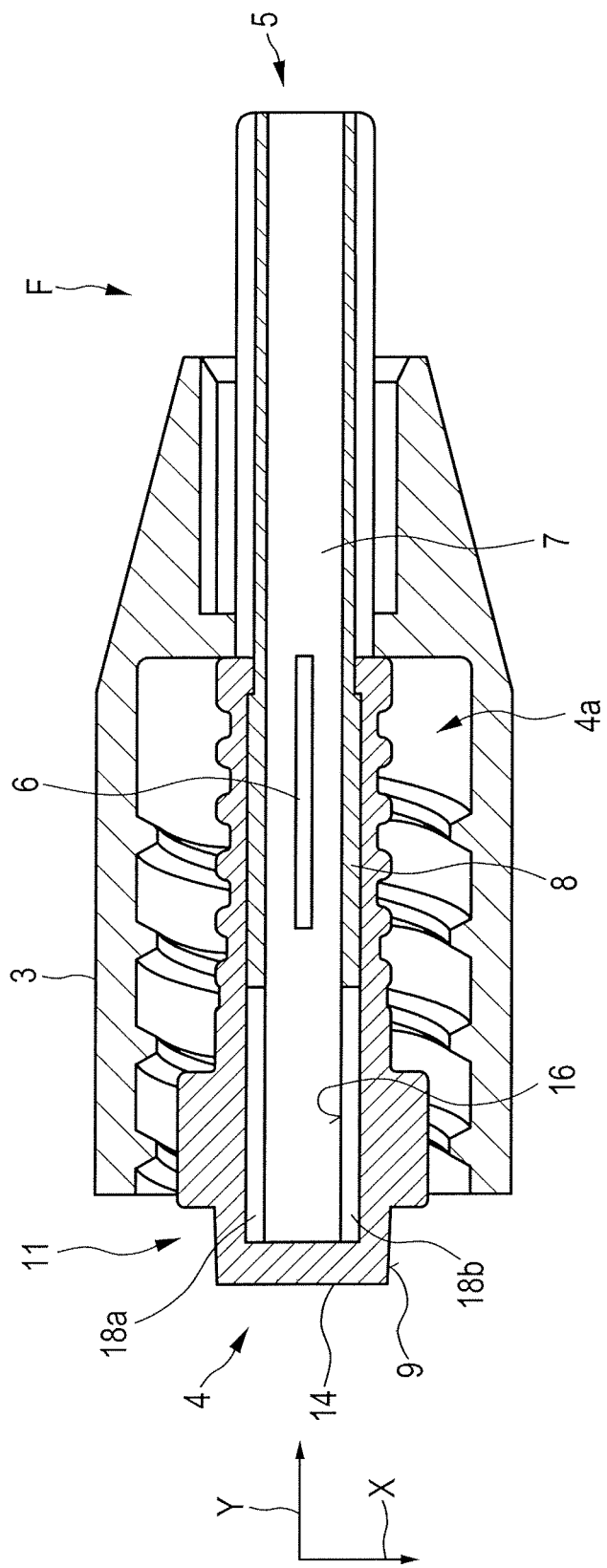
Figure 4B:
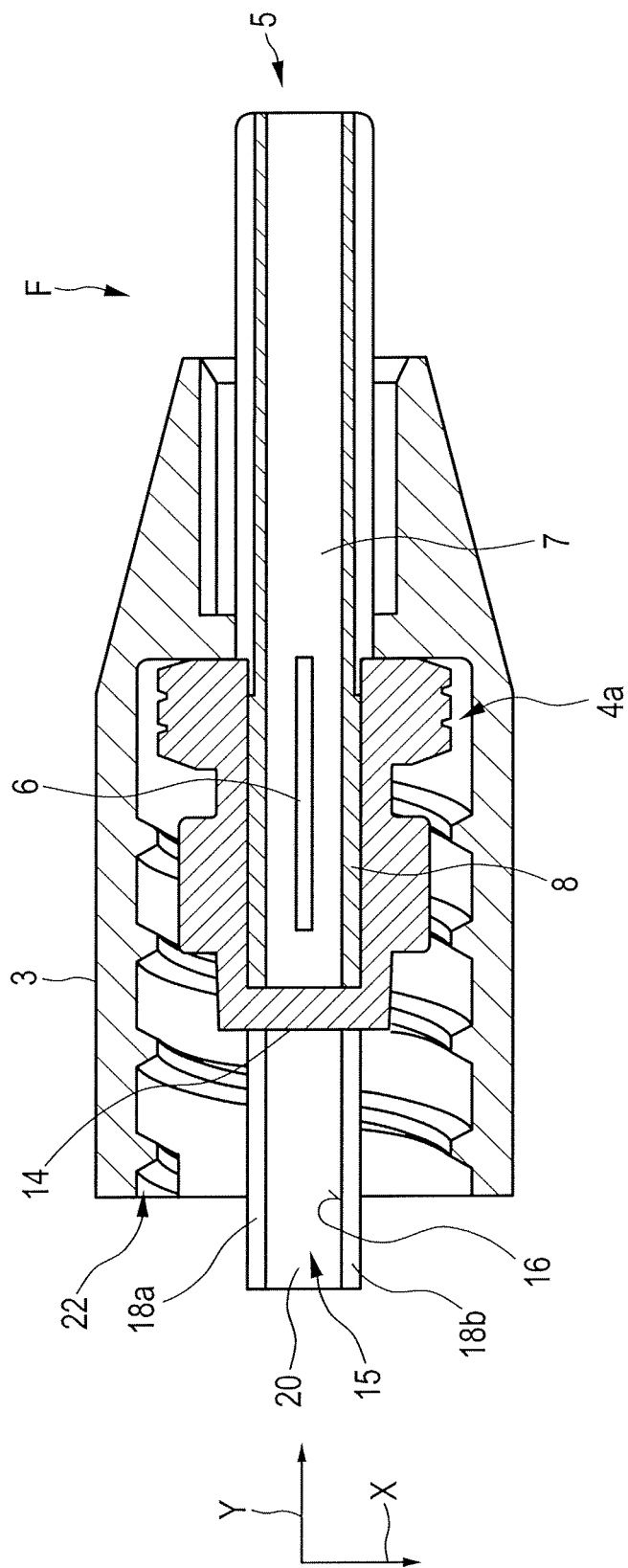
Figure 5:
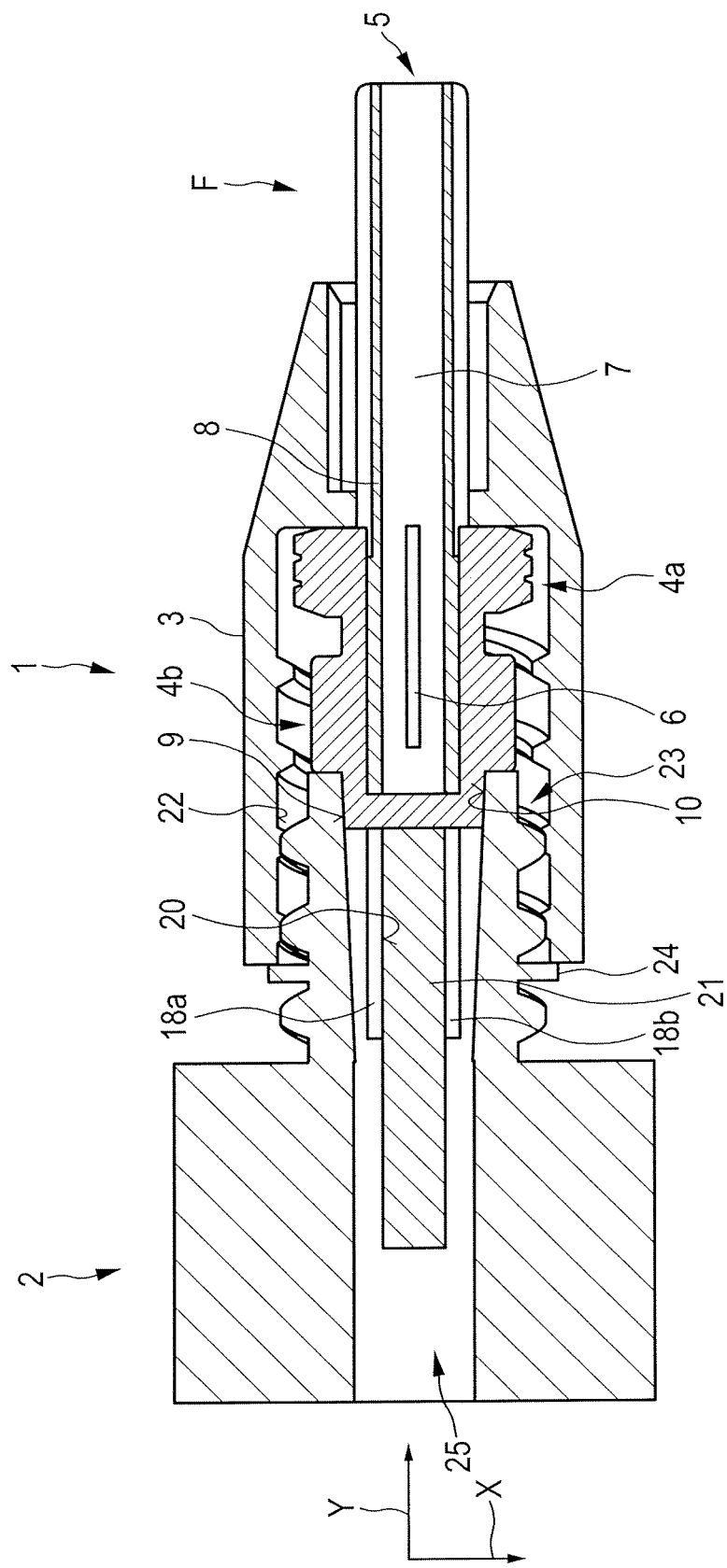

Further advantages and features are derived from the description hereunder of an exemplary embodiment, which is illustrated by means of the drawings, in which:

FIG. 1 in a schematic perspective illustration shows an embodiment of a fluid connection device, which is provided in particular for connecting in a fluid-tight manner hose portions in an infusion therapy;

FIG. 2a in a schematic perspective illustration corresponding to that of FIG. 1 shows a soft elastic sealing member of the fluid connection device as per FIG. 1 in an elastically non-deformed state (sealing position);

FIGS. 2b and 2c show the sealing member as per FIGS. 1 and 2a in a schematic longitudinal sectional illustration in a section plane Y-Z according to FIG. 1, in the elastically non-deformed state (FIG. 2b) and in an elastically compressed state (compression position) (FIG. 2c);

FIGS. 3a and 3b in a schematic longitudinal sectional illustration in a section plane Y-Z according to FIG. 1 show the fluid connection device as per FIG. 1 in a state closed in a fluid-tight manner (FIG. 3a) and in an opened state (FIG. 3b), wherein the sealing member assumes the compression position;

FIGS. 4a and 4b in a further schematic longitudinal sectional illustration in a section plane X-Y according to FIG. 1 show the fluid connection device as per FIGS. 1 and 3a and 3b in a state closed in a fluid-tight manner (FIG. 4a) and in the opened state corresponding to that of FIG. 3b (FIG. 4b); and FIG. 5 in a schematic longitudinal sectional illustration in a section plane X-Y according to FIG. 1 shows the fluid connection device as per FIGS. 1, 3a, 3b, 4a, and 4b in a state connected to a complementary connector unit.

DETAILED DESCRIPTION

A medical fluid connection device 1 as per FIGS. 1 and 3a to 5 is configured in the design of a male Luer connector and is provided for connecting in a fluid-conducting manner two medical hose line portions. For this purpose, the medical fluid connection device 1 in a manner yet to be explained in more detail is connectable in a fluid-tight manner to a complementary connector unit 2 (FIG. 5) which is configured in the design of a female Luer connector.

The fluid connection device 1 is composed of only two components, specifically a housing member 3 and a soft elastic sealing member 4.

The housing member 3 has an inlet opening 5 that is disposed at an end side, and at least one outlet opening 6. The inlet opening 5 and the outlet opening 6 are interconnected in a fluid-conducting manner by way of a fluid duct 7 that extends substantially along an axial direction Y. The inlet opening 5 is disposed on an end-side housing appendage F of the housing member 3, said housing appendage F being provided for connecting in a fluid-tight manner to a medical hose portion (not referred to in more detail). The soft elastic sealing member 4 in the basic shape thereof is configured in the design of a sleeve which in a circumferential direction U at least in portions encompasses a wall 8 of the fluid duct 7 and is guided so as to be movable along the axial direction Y in relation to the wall 8. In other words: the sealing member 4 along the axial direction Y is plug-fitted onto the wall 8 of the fluid duct 7 and to this extent is supported in a radial direction on the wall 8.

As can be seen in particular by means of FIGS. 3a and 4a, the sealing member 4 in a non-connected state of the fluid connection device 1 assumes a sealing position. The sealing member 4 in this sealing position seals the at least one outlet opening 6 in a fluid-tight manner such that a fluid path that extends between the inlet opening 5 and the outlet opening 6 is sealed in a fluid-tight manner. By contrast, the sealing member 4 in a state of the fluid connection device 1 connected to the complementary connector unit 2 assumes a compression position (FIGS. 2c, 3b, 4b, and 5). The sealing member 4 in this compression position along the axial direction Y is elastically compressed in such a manner that the at least one outlet opening 6 and thus the fluid path that extends through the fluid connection device 1 are released.

A Luer external taper 9, known per se, is provided for connecting the fluid connection device 1 in a fluid-tight manner to the connector unit 2. This Luer external taper is provided for receiving a Luer internal taper 10 of the connector unit 2. To this extent, the Luer external taper 9 and the Luer internal taper 10 configure a Luer connection system that in the field of medical technology is known per se.

According to the present disclosure, the Luer external taper 9 is configured by a wall portion 11 of the soft elastic sealing member 4. As can be seen in particular by means of FIGS. 2a to 2c, the wall portion 11 is disposed on the end side of that end of the sealing member 4 that faces away from the inlet opening 5. The wall portion 11 is a wall portion of the sealing member that extends in the circumferential direction U. The wall portion in the axial direction Y is delimited by a radially extending bead B. Moreover, the wall portion 11 comprises two part-wall portions 11a and 11b that are mutually separated in the circumferential direction U, wherein the separation between these two part-wall portions is configured in a manner yet to be explained in more detail. The Luer external taper 9 in the axial direction Y in relation to the non-deformed sealing position of the sealing member 4 extends across approximately ⅕ of the overall length of the sealing member 4 (FIG. 2a).

As can be furthermore seen in particular by means of FIGS. 2a to 2c, the sealing member 4 has a compression portion 4a and a coupling portion 4b. The compression portion 4a in comparison to the coupling portion 4b is designed so as to be thin-walled and, as a consequence of a profiled feature P, has an accordion-type design. In conjunction with the soft elastic material composition of the sealing member 4, which in particular can comprise silicone rubber, the design embodiment of the compression portion 4a in this manner permits an elastic compressibility of the sealing member 4 along the axial direction y adapted to the functionality. By contrast, the coupling portion 4b is embodied so as to be comparatively thick-walled and comprises in particular the Luer external taper 9 and the bead B. The coupling portion 4b in the compression position of the sealing member 4 is substantially non-deformed, whereas the compression portion 4a is compressed to approximately ⅓ of the non-deformed initial length of the latter.

The sealing member 4 furthermore has two passage openings 12a, 12b. It is of course also possible for only one passage opening to be provided on the sealing member 4. The passage opening in the compression position of the sealing member 4 in relation to the at least one outlet opening 6 is disposed so as to at least in portions overlap in such a manner that said at least one outlet opening 6 is released at least in portions, thus causing a fluid-conducting connection between the inlet opening 5 and the two passage openings. The passage openings 12a, 12b are in each case configured in the design of a passage slot. The passage slots 12a, 12b, proceeding from an axial end face E, are incorporated in the wall portion 11 along the axial direction Y. To this extent, the passage openings 12a, 12b subdivide the wall portion 11 into the two part-wall portions 11a and 11b. The passage openings 12a, 12b in the region of the Luer external taper 9, or of the wall portion 11, respectively, are open in the radial direction. The passage openings 12a, 12b in a region adjoining the Luer external taper in the axial direction Y are in each case covered in the radial direction by way of a wall portion 13a, 13b of the sealing member 4, in particular the coupling portion 4b.

In a manner corresponding to the slot-shaped design embodiment of the passage opening 12a, the at least one outlet opening 6 is configured in the design of an outlet slot. Moreover, a second outlet opening 6a which is assigned to the passage opening 12b and is likewise configured in the design of an outlet slot is provided. The two outlet slots 6, 6a, like the passage slots 12a, 12b, are disposed so as to be mutually offset by approximately 180° in the circumferential direction U. The outlet openings 6, 6a extend radially through the wall 8 of the fluid duct 7 and to this extent are configured in the design of in each case one radial opening. The length of the outlet openings 6, 6a in relation to the axial direction Y corresponds to approximately 50% of the non-deformed length of the sealing member 4.

The sealing member 4 moreover has a closure portion 14. The closure portion 14 is configured in the design of a circular-cylindrical stopple and is provided for sealing an end-side axial opening 15 of the fluid duct 7. As can be seen in particular by means of FIGS. 3a and 3b, the closure portion is configured in such a manner that the latter in a repositioning of the sealing member 4 is movable in the fluid duct 7 along the fluid duct 7 between the sealing position and the compression position. In the case of a repositioning of the sealing member 4 in this manner, the closure portion 14 in the radial direction bears on an internal wall 16 of the fluid duct 7 such that the axial opening 15 is permanently sealed.

The sealing member 4 furthermore has two profiled portions 17a, 17b. It is of course also possible for only one profiled portion to be provided. The two profiled portions 17a, 17b are in each case connected in a form-fitting manner to one complementary profiled counter portion 18a, 18b of the housing member 3. The sealing member 4 in the circumferential direction U is fixed to the housing member 3 in this manner. The profiled portions 17a, 17b are in each case configured in the design of a sliding element. Accordingly, the profiled counter portions 18a, 18b are in each case configured in the design of a guide slot that extends in the axial direction Y. The guide slots 18a, 18b, proceeding from that end face of the fluid duct 7 that faces away from the inlet opening 5, are in each case incorporated in the wall 8 of said fluid duct 7. The guide slots 18a, 18b in relation to the axial direction Y extend in each case across a length which corresponds to approximately 50% of the non-deformed length of the sealing member 4. The profiled portions 17a, 17b moreover form in each case a material bond between the closure portion 14 and the Luer external taper 9, or the wall portion 11, respectively. As can further be seen in particular by means of FIG. 2a, the profiled portions 17a, 17b are disposed so as to be mutually offset by 180° in the circumferential direction U. The respective angular offset between the profiled portions 17a, 17b and the passage openings 12a, 12b herein is in each case approximately 90°.

As can furthermore be seen in particular by means of FIG. 5, the fluid duct 7 has a receptacle portion 20. The receptacle portion 20 is provided for receiving an elongate receptacle appendage 21 of the complementary connector unit 2. The receptacle appendage 21 is configured in the design of a circular-cylindrical pin. The external diameter of the receptacle appendage 21 corresponds substantially to an internal diameter of the receptacle portion 20.

The housing member 3 moreover has a threaded portion 22. The threaded portion 22 is configured in the design of an internal thread. The internal thread 22 is provided for connecting to a threaded counter portion 23 in the design of an external thread which is disposed on the connector unit 2 so as to at the end side encompass the receptacle appendage 21.

In order for the medical fluid connection device 1 to be connected in a fluid-conducting manner to the complementary connector unit 2, the Luer internal taper 10 of the connector unit 2 is first brought to bear on the Luer external taper 9 of the fluid connection device. The Luer internal taper 10 herein is plug-fitted in the axial direction Y onto the wall portion 11 of the sealing member 4 until a bearing is established on the bead B of the coupling portion 4b. The threaded counter portion 23 is furthermore screw-fitted to the threaded portion 22, wherein the sealing member 4, proceeding from the sealing position (FIG. 3a, 4a) in the axial direction along the axial direction Y is compressed to the compression position. Moreover, the receptacle appendage 21 in this case enters the receptacle portion 20 of the fluid duct 7 and the closure portion 14 moves, proceeding from the end-side axial opening 15 is of the fluid duct, along the internal wall 16 in the fluid duct 7. The sealing member 4 on account of the engagement of the sliding elements 17a, 17b in the guide slots 18a and 18b, respectively, in the circumferential direction herein is fixed in relation to the housing member 3. A connection according to the function between the fluid connection device 1 and the connector unit 2 is established in a position that is fixed by a thrust bead 24 of the threaded counter portion 23. In said connection the outlet slots 6, 6a are at least in portions released by a respective positioning of the passage slots 12a and 12b, respectively. A fluid-conducting connection between the inlet opening 5, the outlet slots 6, 6a, the passage openings 12, 12b, and a discharge duct 25 of the connector unit 2 is established in this manner. A hose portion (not to be seen in more detail) which in turn can be connected in a fluid-conducting manner to, for example, an infusion container or the like, can be disposed on that end face region of the discharge duct 25 that faces away from the fluid connection device 1. A medical fluid can in this manner make its way, proceeding from the inlet opening 5, to the discharge duct 25, or vice versa.

In order for the fluid connection device 1 to be separated from the connector unit 2, the screw connection between the threaded portion 22 and the threaded counter portion 23 is manually released. As a consequence of the soft elastic design of the sealing member 4 the latter causes a restoring force that is directed along the axial direction Y. To this extent, the sealing member 4 in the removal of the complementary connector unit 2, proceeding from the elastically compressed sealing position, in a self-acting manner assumes the elastically non-deformed sealing position. The fluid path between the inlet opening 5 and the discharge duct 25 is closed in a self-acting manner in this way.

The invention claimed is:

1. A medical fluid connection device for connecting in a fluid-conducting manner to a complementary connector unit, the medical fluid connection device comprising a housing member having an inlet opening and at least one outlet opening, said inlet opening and said at least one outlet opening being interconnected in a fluid-conducting manner by way of a fluid duct that extends substantially along an axial direction, and a soft elastic sealing member which in a circumferential direction at least in portions encompasses a wall of the fluid duct and along the axial direction is guided so as to be movable in relation to the wall of the fluid duct, wherein the sealing member in a non-connected state of the fluid connection device assumes a sealing position and seals in a fluid-tight manner the at least one outlet opening and, in a state of the fluid connection device connected to the complementary connector unit, along the axial direction is elastically compressed to a compression position in such a manner that the at least one outlet opening is released, wherein a Luer external taper is provided for connecting in a fluid-tight manner to a Luer internal taper of the complementary connector unit, wherein the Luer external taper is configured by a wall portion of the soft elastic sealing member, the sealing member defining at least one passage opening extending radially through a sidewall of the sealing member, the at least one passage opening positioned to overlap said at least one outlet opening at least in portions when the sealing member is in the compression position such that said at least one outlet opening is released at least in portions, causing a fluid-conducting connection between the inlet opening and the at least one passage opening.

2. The medical fluid connection device according to claim 1, wherein the at least one passage opening comprises a pair of diametrically opposed passage openings through the sidewall of the sealing member.

3. The medical fluid connection device according to claim 1, wherein the at least one passage opening is configured in the design of a passage slot, and/or the at least one outlet opening is configured in the design of an outlet slot.

4. The medical fluid connection device according to claim 1, wherein the at least one outlet opening extends in a substantially radial manner through the wall of the fluid duct.

5. The medical fluid connection device according to claim 1, wherein the sealing member has a closure portion which in a fluid-tight manner seals an end-side axial opening of the fluid duct.

6. The medical fluid connection device according to claim 1, wherein the sealing member has a profiled portion which is connected in a form-fitting manner to a complementary profiled counter portion of the housing member in such a manner that the sealing member in the circumferential direction is fixed to the wall of the fluid duct.

7. The medical fluid connection device according to claim 1, wherein the fluid duct has a receptacle portion which is provided for receiving an elongate receptacle appendage (of the complementary connector unit.

8. The medical fluid connection device according to claim 1, wherein the housing member has a threaded portion which is provided for connecting to a threaded counter portion of the complementary connector unit.

9. The medical fluid connection device according to claim 1, wherein said medical fluid connection device consists of the sealing member and the housing member.

10. A medical fluid connection device for connecting in a fluid-conducting manner to a complementary connector unit, the medical fluid connection device comprising a housing member having an inlet opening and at least one outlet opening, said inlet opening and said at least one outlet opening being interconnected in a fluid-conducting manner by way of a fluid duct that extends substantially along an axial direction, and a soft elastic sealing member which in a circumferential direction at least in portions encompasses a wall of the fluid duct and along the axial direction is guided so as to be movable in relation to the wall of the fluid duct, wherein the sealing member in a non-connected state of the fluid connection device assumes a sealing position and seals in a fluid-tight manner the at least one outlet opening and, in a state of the fluid connection device connected to the complementary connector unit, along the axial direction is elastically compressed to a compression position in such a manner that the at least one outlet opening is released, wherein a Luer external taper is provided for connecting in a fluid-tight manner to a Luer internal taper of the complementary connector unit, wherein the Luer external taper is configured by a wall portion of the soft elastic sealing member, wherein the sealing member has a closure portion which in a fluid-tight manner seals an end-side axial opening of the fluid duct, and wherein the closure portion is configured in such a manner that said closure portion in a repositioning of the sealing member is movable in the fluid duct along the fluid duct between the sealing position and the compression position.

11. A medical fluid connection device for connecting in a fluid-conducting manner to a complementary connector unit, the medical fluid connection device comprising a housing member having an inlet opening and at least one outlet opening, said inlet opening and said at least one outlet opening being interconnected in a fluid-conducting manner by way of a fluid duct that extends substantially along an axial direction, and a soft elastic sealing member which in a circumferential direction at least in portions encompasses a wall of the fluid duct and along the axial direction is guided so as to be movable in relation to the wall of the fluid duct, wherein the sealing member in a non-connected state of the fluid connection device assumes a sealing position and seals in a fluid-tight manner the at least one outlet opening and, in a state of the fluid connection device connected to the complementary connector unit, along the axial direction is elastically compressed to a compression position in such a manner that the at least one outlet opening is released, wherein a Luer external taper is provided for connecting in a fluid-tight manner to a Luer internal taper of the complementary connector unit, wherein the Luer external taper is configured by a wall portion of the soft elastic sealing member, wherein the sealing member has a profiled portion which is connected in a form-fitting manner to a complementary profiled counter portion of the housing member in such a manner that the sealing member in the circumferential direction is fixed to the wall of the fluid duct, and wherein the profiled portion has at least one sliding element which engages in a guide slot of the profiled counter portion.

* * * * *